US010674810B2

(12) United States Patent
Bloch (10) Patent No.: US 10,674,810 B2
(45) Date of Patent: Jun. 9, 2020

(54) ORAL CARE IMPLEMENT COMPRISING MIRROR AND LIGHT DISTRIBUTIVE ELEMENT, AND METHOD OF FORMING THE SAME (71) Applicant: COLGATE-PALMOLIVE COMPANY, New York, NY (US)

(72) Inventor: Brian Bloch, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 493 days.

(21) Appl. No.: 14/654,526

(22) PCT Filed: Mar. 18, 2013

(86) PCT No.: PCT/US2013/032756
§ 371 (c)(1),
(2) Date: Jun. 20, 2015

(87) PCT Pub. No.: WO2014/098947
PCT Pub. Date: Jun. 26, 2014

(65) Prior Publication Data
US 2015/0342337 A1 Dec. 3, 2015

(30) Foreign Application Priority Data
Dec. 21, 2012 (CN) .......................... 2012 1 0599109

(51) Int. Cl.
A61B 1/247 (2006.01)
A46B 15/00 (2006.01)
A61C 17/34 (2006.01)

(52) U.S. Cl.
CPC ...... A46B 15/0036 (2013.01); A46B 15/0077 (2013.01); A46B 15/0081 (2013.01);
(Continued)

(58) Field of Classification Search
CPC ............ A46B 15/0036; A46B 15/0044; A46B 15/0077; A46B 15/0081; A61B 1/247
See application file for complete search history.

(56) References Cited

U.S. PATENT DOCUMENTS 2,241,584 A * 5/1941 Cohen ...................... A46B 9/04
132/309
D326,189 S * 5/1992 Brooks .......................... D4/108
(Continued)

FOREIGN PATENT DOCUMENTS

EP 1101436 5/2001
RU 2411580 C2 3/2006
(Continued)

OTHER PUBLICATIONS http://gulfbusiness.tradeholding.com/default.cgi/action/viewproducts/productid/41749/productname/Toothbrush with light and mirror/ 2 pp, date unknown but prior to the date of this application.
(Continued)

Primary Examiner — Yogesh P Patel
Assistant Examiner — Jennifer F Gill (57) ABSTRACT An oral care implement, such as a toothbrush, that comprises a mirror and a light pipe adjacent the mirror. In one embodiment, the invention can be an oral care implement comprising: a body comprising a handle portion and a head portion; a mirror coupled to the body; a light source coupled to the body; and a light pipe coupled to the body and surrounding at least a portion of the mirror, the light pipe operably coupled to the light source to distribute light emitted by the light source through the light pipe.

20 Claims, 5 Drawing Sheets (52) U.S. Cl.
CPC ...... *A61B 1/247* (2013.01); *A46B 2200/1066* (2013.01); *A61C 17/3481* (2013.01); *Y10T 29/49568* (2015.01)

(56) References Cited

U.S. PATENT DOCUMENTS

| | | | | |
|---|---|---|---|---|
| 5,324,129 | A * | 6/1994 | Root | A46B 7/02 132/309 |
| 5,873,207 | A * | 2/1999 | Bertels | E01F 8/0023 52/250 |
| 6,202,242 | B1 * | 3/2001 | Salmon | A46B 5/00 15/105 |
| 6,412,137 | B1 * | 7/2002 | Heidari | A46B 9/12 15/105 |
| 6,902,397 | B2 * | 6/2005 | Farrell | B08B 7/0057 15/167.1 |
| 7,223,270 | B2 * | 5/2007 | Altshuler | A46B 15/0002 433/29 |
| 7,467,946 | B2 * | 12/2008 | Rizoiu | A46B 5/002 433/29 |
| 2005/0000049 | A1 * | 1/2005 | Hohlbein | A46B 9/026 15/111 |
| 2006/0057087 | A1 | 3/2006 | Moskovich et al. | |
| 2007/0111168 | A1 * | 5/2007 | Ribal | A46B 15/0077 433/216 |
| 2007/0271714 | A1 * | 11/2007 | Adam | A61C 17/222 15/22.2 |
| 2008/0276393 | A1 * | 11/2008 | Russell | A46B 7/00 15/105 |
| 2008/0276398 | A1 * | 11/2008 | Nanda | A46B 15/0002 15/167.1 |
| 2009/0091178 | A1 | 4/2009 | Waguespack et al. | |
| 2010/0043161 | A1 * | 2/2010 | Tanuma | A46B 15/0002 15/106 |
| 2010/0178252 | A1 * | 7/2010 | Sagel | A61B 5/0088 424/9.6 |
| 2010/0325828 | A1 * | 12/2010 | Braun | A46B 15/0002 15/167.1 |
| 2011/0232015 | A1 * | 9/2011 | Nanda | A46B 15/0002 15/167.1 |
| 2012/0198643 | A1 * | 8/2012 | Jungnickel | A46B 9/04 15/167.1 |
| 2013/0143430 | A1 * | 6/2013 | Sorolla Rosario | H01R 13/005 439/485 |

FOREIGN PATENT DOCUMENTS

| | | | |
|---|---|---|---|
| WO | WO 99/12448 | | 3/1999 |
| WO | WO 2007/003237 A1 | | 1/2007 |
| WO | WO 2007106955 | * | 3/2007 |
| WO | WO 2007/106955 | | 9/2007 |
| WO | WO 2007/111703 A2 | | 10/2007 |

OTHER PUBLICATIONS

International Search Report and the Written Opinion of the International Searching Authority issued in International Patent Application PCT/US2013/032756 dated Jul. 29, 2013.

Written Opinion of the International Preliminary Examining Authority issued in International Patent Application PCT/US2013/032756 dated Mar. 9, 2015.

* cited by examiner

ORAL CARE IMPLEMENT COMPRISING MIRROR AND LIGHT DISTRIBUTIVE ELEMENT, AND METHOD OF FORMING THE SAME

CROSS-REFERENCE TO RELATED PATENT APPLICATIONS

This application is a U.S. national stage application under 35 U.S.C. § 371 of PCT Application No. PCT/US2013/032756, filed Mar. 18, 2013, which claims priority to Chinese Patent Application No. 201210599109.2, filed Dec. 21, 2012, the entireties of which are incorporated herein by reference.

BACKGROUND OF THE INVENTION

During an oral care session, a user may want to view certain areas of the oral cavity. However, it is difficult for a user to view his/her own oral cavity due to the oral cavity's darkened nature, even when the user is looking in a mirror. Furthermore, even if the oral care cavity is adequately illuminated, certain areas of the oral care cavity are still not visible when looking in a mirror. In order to view such areas a second mirror must be inserted within the oral cavity for viewing through the first mirror. The insertion of a second mirror into the oral cavity, however, may obstruct the required illumination or the user's view in certain circumstances.

While toothbrushes that include both a mirror and a light source are known, these toothbrushes are less than optimal as the light generated by the light source is not adequately distributed. Rather, the light generated by these known toothbrushes tends to be overly bright and focused in a very specific area. Moreover, in known toothbrushes that include a light source and a mirror, the light source is exposed. As a result, the light source can come into direct contact with the oral surfaces of the user during use. Thus, in such toothbrushes, if the light source were to become hot due to prolonged illumination, there is the danger of burning the user's oral surfaces during use thereof.

Therefore, a need exists for an oral care implement having a mirror and a light source that distributes light emitted by the light source and/or protects the oral cavity from heat generated by the light source.

BRIEF SUMMARY OF THE INVENTION

An oral care implement, such as a toothbrush, that comprises a mirror and a light pipe adjacent the mirror. The light pipe, in certain embodiments, can distribute light generated by a light source about the perimeter of the mirror to increase the ability of the user to see oral surfaces using the mirror.

In one embodiment, the invention can be an oral care implement comprising: a body comprising a handle portion and a head portion; a mirror coupled to the body; a light source coupled to the body coupled to the body adjacent the mirror; and a light transmissive elastomeric material coupled to the body and overlying the light source.

In another embodiment, the invention can be an oral care implement comprising: a body comprising a handle portion and a head portion; a mirror coupled to the body; a light source coupled to the body; and a light pipe coupled to the body and surrounding at least a portion of the mirror, the light pipe operably coupled to the light source to distribute light emitted by the light source through the light pipe.

In another embodiment, the invention can be a method of forming an oral care implement comprising: a) forming a body comprising a handle portion and a head portion; b) coupling a light source to the body; c) coupling a mirror to the body adjacent the light source; and d) coupling a light pipe to the body adjacent the mirror in operable coupling with the light source.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring to FIGS. 1-4 concurrently, an oral care implement 100 according to an embodiment of the present invention is illustrated. While the oral care implement 100 is exemplified as a toothbrush, in other embodiments, the oral care implement can take the form of a soft-tissue cleansing implement, an inter-proximal pick, a flossing tool, a plaque scraper, a powered toothbrush, or other ansate implement designed for oral care. It is also to be understood that other embodiments may be utilized, and that structural and functional modifications may be made without departing from the scope of the present invention.

The oral care implement 100 comprises a handle 110 and a head 120. The handle 110 provides the user with a mechanism by which he/she can readily grip and manipulate the oral care implement 100. The head 120 is connected to a distal end 111 of the handle 110 and includes a plurality of teeth cleaning elements 130 extending therefrom, which are generically illustrated. The oral care implement 100 extends from a proximal end 101 (which is also the proximal end of the handle 110) to a distal end 102 along a longitudinal axis A-A (illustrated in FIG. 2). Conceptually, the longitudinal axis A-A is a reference line that is generally coextensive with the three-dimensional center line of the handle 110 and the head 120. Because in certain embodiments the handle 110 is a non-linear structure, the longitudinal axis A-A for the oral care implement 100 is also non-linear in such embodiments. However, in certain other embodiments, the oral care implement 100 has a linear arrangement and, thus, has a substantially linear longitudinal axis A-A.

The oral care implement 100 comprises a body 150, which is the primary structural component of the oral care implement 100 to which the additional components are coupled or housed herein. The body 150 generally comprises a head portion 151 and a handle portion 152. The head portion 151 of the body 150 serves as the structural base for the head 120 of the oral care implement 100 while the handle portion 152 of the body 150 serves as the structural base for the handle 110 of the oral care implement 100. The body 150, in one embodiment, is constructed of a rigid material, such as for example a hard plastic. Suitable hard plastics include without limitation polyethylene, polypropylene (PP), polyamide, polyester, cellulosic, SAN, acrylic, ABS or any other of the commonly known thermoplastics used in toothbrush manufacture.

The head portion 151 is coupled to the handle portion 152 at the distal end 111 thereof (which is also the distal end 111 of the handle 110). In one embodiment, the head portion 151 and the handle portion 152 of the body 150 are formed as an integral structure using an injection molding process. In other embodiments, however, the handle portion 152 and the head portion 151 of the body 150 may be formed as separate components which are coupled together at a later stage of the manufacturing process by any suitable technique known in the art, including without limitation thermal welding, sonic welding, a tight-fit assembly, a coupling sleeve, adhesion, or fasteners. Whether the head portion 151 and the handle portion 152 are constructed as a single integral component or a multi-piece assembly (including connection techniques) is not limiting of the present invention in all embodiments, unless specifically recited in the claims. Furthermore, other manufacturing techniques may be used in place of and/or in addition to injection molding to create the body 150 (including the handle portion 151 and/or the head portion 152), such as milling and/or machining.

The oral care implement 100 generally comprises the body 150, a mirror 20 coupled to the body 150, a light source 30 coupled to the body 150, and a light pipe 40 coupled to the body 150 adjacent the mirror 20 and operably coupled to the light source 30. In the exemplified embodiment, the mirror 20 and the light pipe 40 are coupled to the head portion 151 of the body 150. More specifically, in the exemplified embodiment, the mirror 20 is coupled to a rear of the head portion 151 so that a reflective surface 21 of the mirror 20 forms a portion of the rear surface 122 of the head 120 of the oral care implement 100. Similarly, the light pipe 40 is coupled to a rear of the head portion 151 of the body 150 so that an outer surface 41 of the light pipe 40 also forms a portion of the rear surface 122 of the head 120. In certain other embodiments, however, the mirror 20 and/or the light pipe 40 are coupled to the body 150 adjacent one another at other locations on the body 150. In one such embodiment, the mirror 20 and/or the light pipe 40 are coupled to the handle portion 152 of the body 150 rather than the head portion 151.

Figure 1:
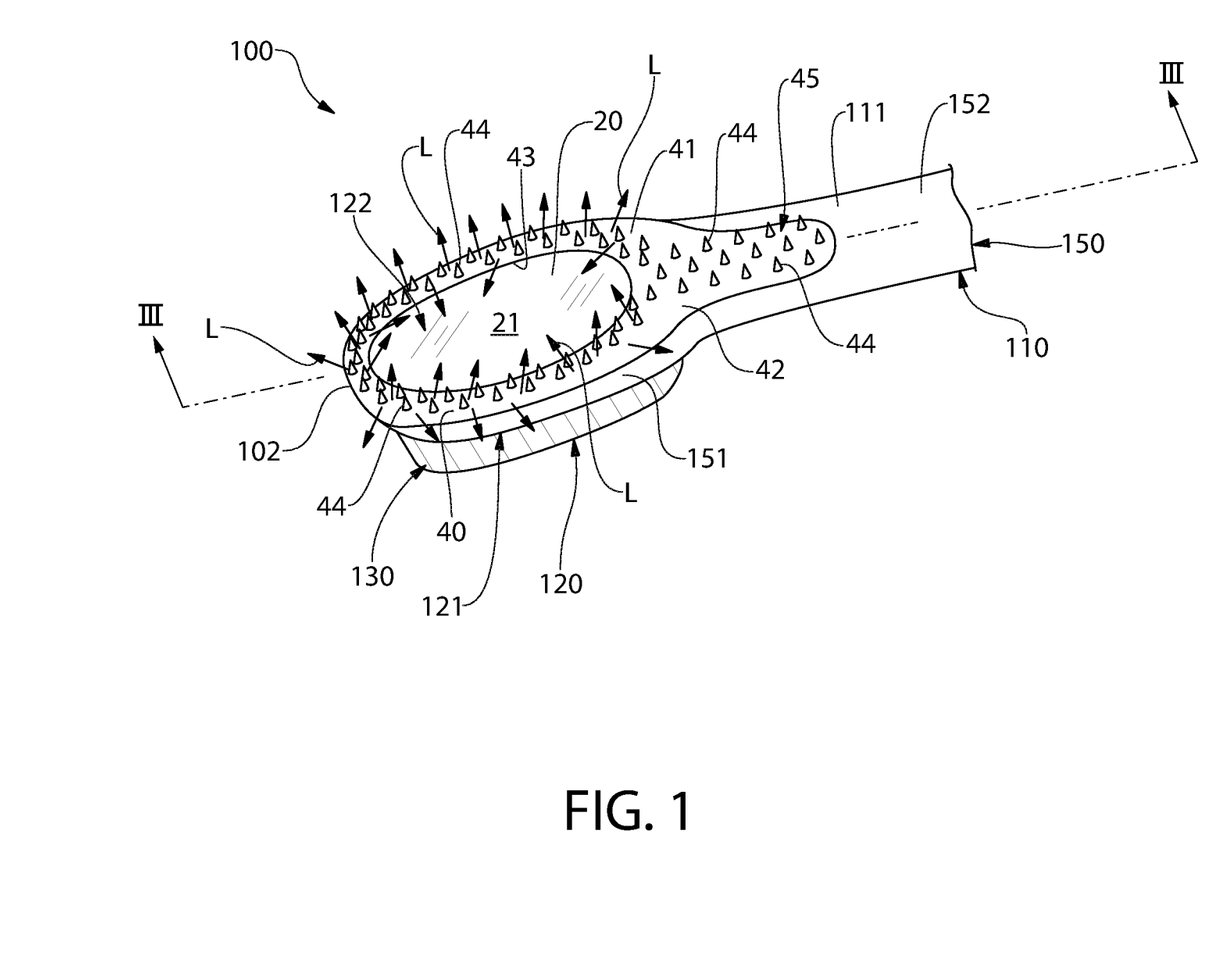
FIG. 1 is a rear perspective view of a head of an oral care implement according to an embodiment of the present invention.
Figure 2:
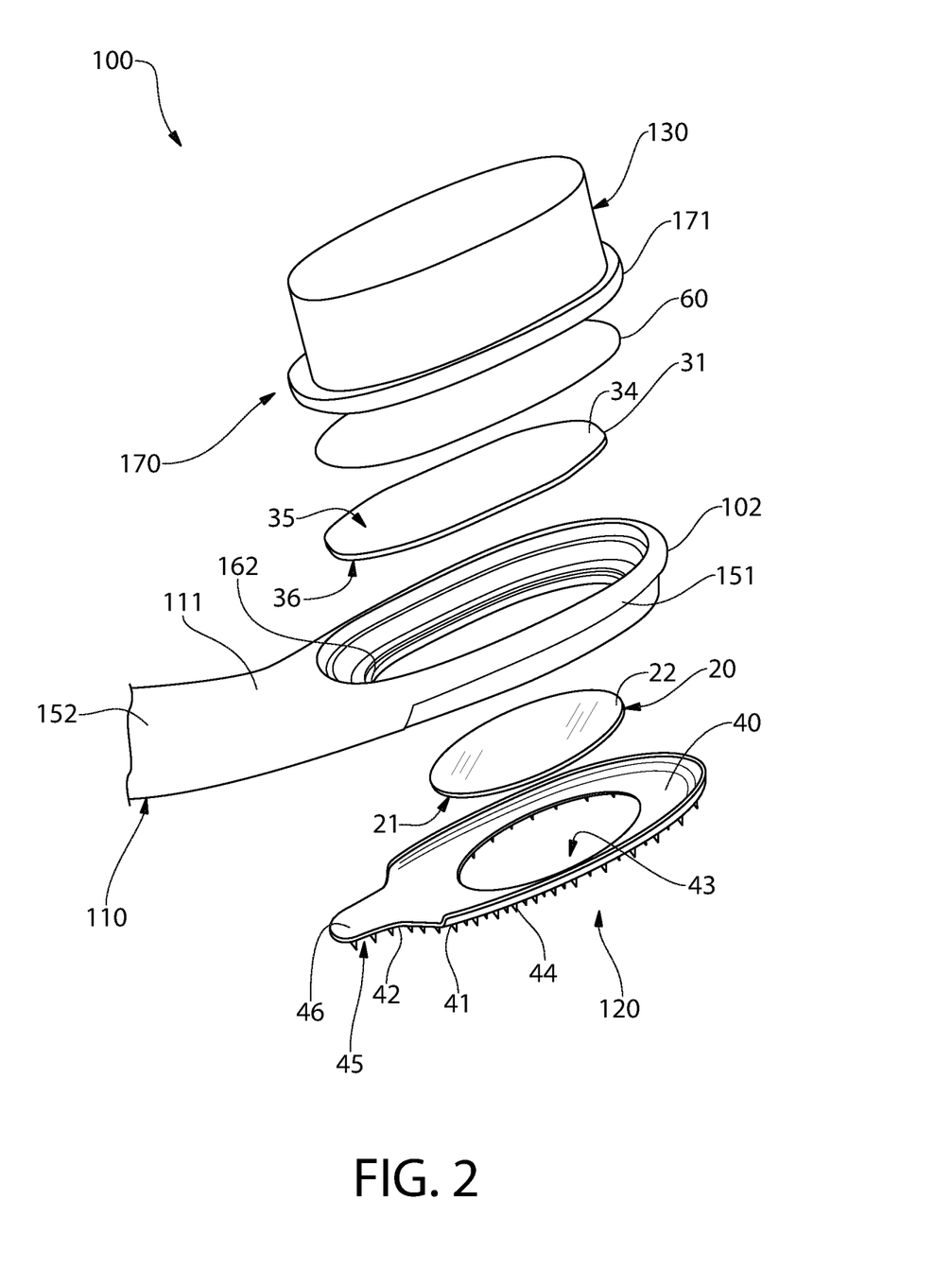
FIG. 2 is an exploded view of the head of the oral care implement of FIG. 1.

The light pipe 40 is operably coupled to the light source 30 so that light L emitted (or generated) by the light source 30 is distributed through the light pipe 40 (described in greater detail below and identified in FIGS. 1 and 4 as arrows L). Thus, in certain embodiments, the light emitted by the light source 30 will be distributed along the length (or portion thereof) of the light pipe 40 to create a greater area of illumination than would otherwise be achieved by the light source 30 absent the light pipe 40. Distribution of the light emitted by the light source 30 can be along a substantial entirety of the light pipe 40 in certain embodiments, or can be along only a portion of the light pipe 40 in other embodiments.

In the exemplified embodiment, the light pipe 40 is formed by a light transmissive elastomeric material 42. In one embodiment, the light transmissive elastomeric material 42 is transparent. In another embodiment, the light transmissive elastomeric material 42 is translucent. Suitable materials for forming the light transmissive elastomeric material 42 include any biocompatible resilient material suitable for uses in an oral hygiene apparatus, such as thermoplastic elastomer. To provide optimum comfort as well as cleaning benefits, the light transmissive elastomeric material 42 preferably has a hardness property in the range of A8 to A25 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used.

In certain embodiments, light refractive particles can be included in the light transmissive elastomeric material 42 to provide enhanced dispersion of light through and from the light transmissive elastomeric material 42 during use. In one embodiment in which a TPE is used to create the light pipe 40, the light pipe 40 can be coupled to the body 150 by overmolding the light transmissive elastomeric material 42 to the body 150 in the appropriate shape to form the light pipe 40.

In one embodiment, the light transmissive elastomeric material 42 that forms the light pipe 40 is a single unitary mass that is formed integrally, using a technique such as injection molding. It should be noted that in certain embodiments, the invention is directed to the use of the light transmissive elastomeric material 42 to overlie the light source 30 adjacent the mirror 20 irrespective of whether the light transmissive elastomeric material 42 is conceptually considered a light pipe. For such embodiments, it is to be understood that the discussion below regarding the shape, structure and structural cooperation of the light pipe 40 is equally applicable to the light transmissive elastomeric material 42.

In other embodiments, the light pipe 40 may be formed of a material other than a light transmissive elastomeric material 42. For example, in one embodiment, the light pipe 40 can be formed of a light transmissive thermoplastic, including transparent or translucent hard plastics. Suitable light transmissive hard plastics include, without limitation, transparent or translucent versions of polyethylene, polypropylene (PP), polyamide, polyester, cellulosic, SAN, acrylic, ABS or any other of the commonly known thermoplastics used in toothbrush manufacture. In one such embodiment, the light pipe 40 is integrally formed with the body 150 and, thus, would be considered as being "coupled to the body 150" during the formation process of the body 150, which can be an injection molding process. In still other embodiments, the light pipe 40 can comprise fiber optics, crystalline materials, or any other material or combination of materials capable of distributing light. In embodiments of the invention, the light pipe 40 can be coupled to the body 150 by adhesion, thermal coupling, sonic welding, overmolding, a snap-fit assembly, a tight-fit assembly, combinations thereof, or other connection techniques that would be known to those of skill in the art. The exact coupling technique will depend on the type of light pipe being used and the material of construction of the light pipe 40 and the body 150.

As mentioned above, the light pipe 40 is located adjacent the mirror 20. In the exemplified embodiment, the light pipe 40 circumferentially surrounds the mirror 20 and, thus, forms an annular frame about the mirror 20. Thus, the light pipe 40, in certain such embodiments, will be (or comprise) a ring that circumferentially surrounds the mirror 20. In the exemplified embodiment in which the light pipe 40 is formed by the light transmissive elastomeric material 42, the light transmissive elastomeric material 42 comprises a ring of the light transmissive elastomeric material 42 that defines a central opening 43 through which the mirror 20 is exposed. In certain other embodiments, however, the light pipe 40 may not fully surround the mirror 20. For example, in one such embodiment, the light pipe 40 circumferentially surrounds only a portion of the mirror 20. In an embodiment where the light pipe 40 is formed of the light transmissive elastomeric material 42, the light transmissive elastomeric material 42 circumferentially surrounds only a portion of the mirror 20, and not the entirety thereof. In another such embodiments, the light pipe 40 may be located only on one side of the mirror 20.

Figure 4:
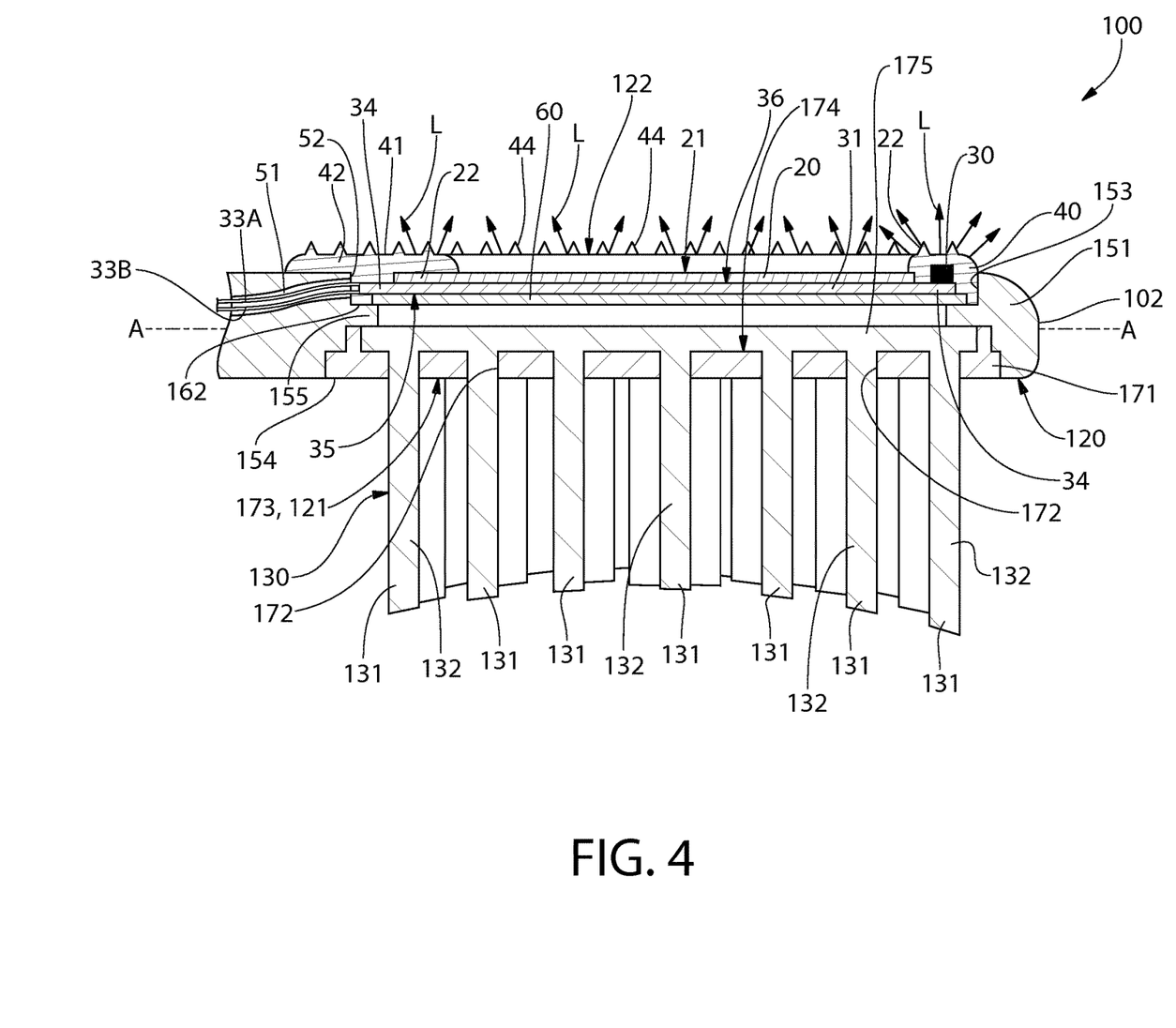
FIG. 4 is a close-up view of area IV-IV of FIG. 3.

As can best be seen in FIG. 4, the light pipe 40, which is formed by the light transmissive elastomeric material 42 in the exemplified embodiment, overlies a perimeter portion 22 of the mirror 20. Overlying the perimeter portion 22 of the mirror 20 with the light pipe 40 may serve two purposes: (1) the light pipe 40 will assist in securing the mirror 20 to the body 150; and/or (2) the perimeter portion 22 of the mirror 20 will serve to reflect light traveling inward back outward so that more light L is leaked from the outer surface 41 of the light pipe 40, thereby further enhancing the illumination effect of the light pipe 40. Increased distribution of light L along the light pipe 40 may be further enhanced by making the outer surface 41 of the light pipe 40 convex in certain embodiments. In one embodiment, the light pipe 40 has a transverse cross-section such that the outer surface 41 of the light pipe 40 is semi-circular. The light pipe 40, in one embodiment, is a solid pipe while, in another embodiment, the light pipe 40 is a hollow pipe.

In the exemplified embodiment, the light source 30 is embedded in the portion of the light transmissive elastomeric material 42 that forms the light pipe 40. In other embodiments, however, the light source 30 may not be embedded in the portion of the light transmissive elastomeric material 42 that forms the light pipe 40. In one such embodiment, the portion of the light transmissive elastomeric material 42 that forms the light pipe 40 merely overlies the light source 30, which may be located within a socket or other depression or cavity in the body 150.

The light pipe 40 further comprises a plurality of protuberances 44 extending from the outer surface 41 of the light pipe 40. The plurality of protuberances 44 are provided so that the light pipe 40 can also be used to cleanse soft tissue in addition to illuminating oral surfaces. In the exemplified embodiment, the plurality of protuberances 44 are nubs. In one embodiment, the plurality of protuberances 44 are conical nubs. As used herein a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection). The base width can be substantially larger than the height.

The plurality of protuberances 44 are designed to significantly reduce a major source of bad breath in people and improve hygiene. The plurality of protuberances 44 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, the plurality of protuberances 44 provide for gentle engagement with the soft tissue while reaching downward into the recesses of adjacent papillae of the tongue.

In other embodiments, the plurality of protuberances 44 can take the form of ribs, flaps, ridges, raise edges, or combinations thereof. While not being limited to such cases, the inclusion of the plurality of protuberances 44 on the light pipe 40 is particularly useful when the light pipe 40 is formed by the light transmissive elastomeric material 42.

In the exemplified embodiment, the plurality of protuberances 44 form a ring about the mirror 20 to maximize soft tissue cleansing effect. As can best be seen in FIGS. 1 and 2, an additional soft tissue cleansing area 45 comprising protuberances 44 is also provided on the rear surface 122 of the head 120. In the exemplified embodiment, this additional soft tissue cleansing area 45 comprises a pad 46 of the light transmissive elastomeric material 42 that also forms the light pipe 40. A plurality of the protuberances 44 extend from the pad 46. In one such embodiment, the pad 46, the plurality of protuberances 44, and the light pipe 40 are integrally formed by a single mass of the transmissive elastomeric material 42 such, for example, during an injection molding process.

In the exemplified embodiment, the mirror 20 is a plate structure. In one embodiment, the mirror 20 is a metal or metallic plate having a highly polished surface that forms the reflective surface 21. Suitable metals include, without limitation, stainless steel silver, aluminum, and bronze, with stainless steel being preferred in certain embodiments due to cost. In other embodiments, the mirror 20 can be a substrate, such as glass, comprising an appropriate reflective layer. In still other embodiments the mirror 20 may be a metal or metallic foil, which can be applied to a substrate or to the body 150 itself.

Figure 5:
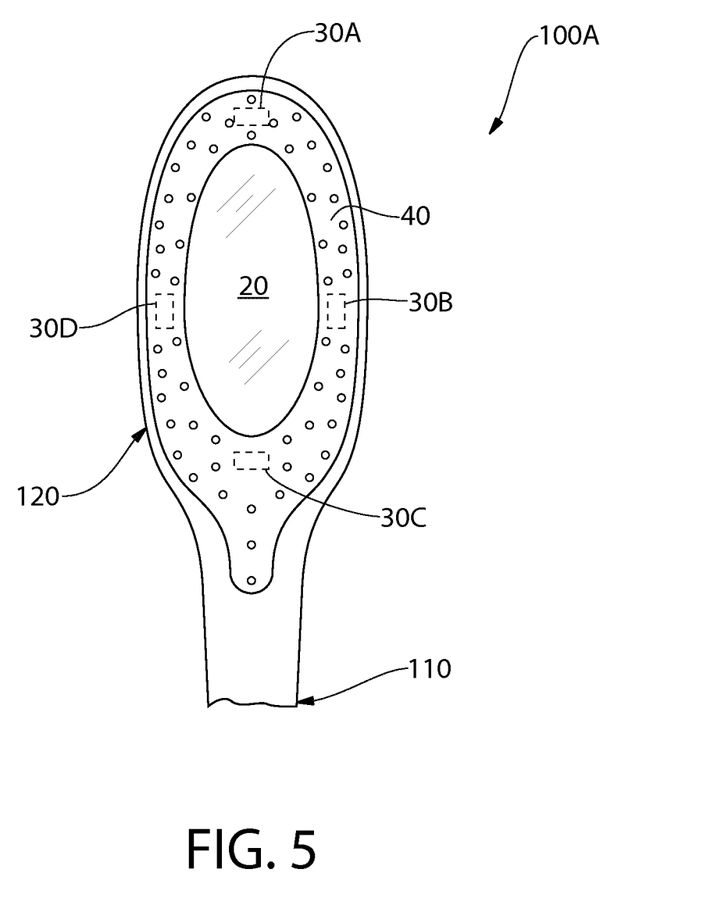
FIG. 5 is a rear view of a head of an oral care implement according to another embodiment of the present invention.

The light source 30, in the exemplified embodiment is a light emitting diode (LED). However, in other embodiments, the light source 30 can be a bulb or other light emitting device as is known in the art. The light source 30 is operably coupled to a printed circuit board (PCB) 31 in the exemplified embodiment. The PCB 31 acts a foundational substrate for the light source 30 and includes the required electrical circuitry and components required to illuminate the light source when power is supplied from a power source 32 to the PCB 31 via electrical wires 33A-B. The PCB 31 is located below the mirror 20 in FIG. 5, wherein the oral care implement 100 is oriented so that a front surface 121 of the head 120 is below a rear surface 122 of the head 120. A portion 34 of the PCB 31 extends beyond the perimetric edge of the mirror 20. The light source 30 is located on the portion 34 of the PCB 31 that extends beyond the mirror 20. As such, the mirror 20 does not block the light emitted by the light source 30. In the exemplified embodiment, the oral care implement 100 includes only a single light source 30 whose light is distributed along the light pipe 40. In one such embodiment, the light pipe 40 distributes the light emitted from the light source 30 at least 1800 (angular) about the perimeter of the mirror 20. However, in other embodiments, such as in the oral care implement 100A shown in FIG. 5, a plurality of light sources 30A-D are provided about the perimeter of the mirror 20 in a circumferentially equi-spaced apart manner. In the embodiment of FIGS. 1-4, the light source 30 is located on the longitudinal axis A-A and between the mirror 20 and the distal end 102 of the head portion 151 of the body 150.

The oral care implement 100 also comprises a seal layer 60 beneath the PCB 31 that seals a front surface 35 of the PCB 31. The seal layer 60 can be formed of a thermoplastic, thermoset, rubber, or other material used for sealing surfaces. The seal layer 60, in one embodiment, is formed of a thermoplastic elastomer, such as those described above for the light transmissive elastomeric material 42. The seal layer 60 seals the front surface 35 of the PCB 30 so that moisture that may be introduced into the head portion 151 is prohibited from contacting the PCB 30. In certain embodiments, the seal layer 60 may also form a seal with the head portion 151 of the body 50. In certain embodiments, however, the seal layer 60 may be omitted if desired. Moreover, in certain embodiments, the PCB 31 may not be necessary depending on the type of light source 30 utilized.

The mirror 20, the PCB 30 and the seal layer 60 are arranged in a stack. More specifically, the PCB 31 is positioned atop the seal layer 60 and the mirror 20 is positioned atop the PCB 31. In certain embodiments, intervening layers may be provided. For example, in one embodiment, a second seal layer is provided between the PCB 31 and the mirror 20 and seals a rear surface 36 of the PCB 31. However, in the exemplified embodiment, the light pipe 40 seals the rear surface 36 of the PCB 31. More specifically, in the exemplified embodiment, the light transmissive elastomeric material 42 that forms the light pipe 40 also seals the rear surface 36 of the PCB 31.

The body 150 of the oral care implement 100 further comprises a rear basin 153 formed in the head portion 151 of the body 150 and a front basin 154 formed in the head portion 151 of the body 150. In the exemplified embodiment, the rear basin 153 and the front basin 154 collectively form a through-hole 155 in the head portion 151 of the body 150. As a result of the through-hole 155, the head portion 151 is an annular structure. In other embodiments, however, a through-hole may not be formed in the head portion 151 and each of the front and rear basins 154, 153 may have a floor formed by a plate portion of the head portion 151 of the body 150. As will be discussed below, the front basin 154 is provided to receive a portion of a head plate assembly 170 when the plurality of cleaning elements 130 are mounted to the head portion 151 using an anchor free tufting (AFT) technique. In embodiments in which AFT is not used, the front basin 154 may be omitted. In still another embodiment, the rear basin 153 may be omitted and the mirror 20, PCB 31 and seal layer 60 may be positioned atop a rear surface of the head portion 151 and coupled thereto.

In the exemplified embodiment, the stack of the seal layer 160, the PCB 31 and the mirror 20 is nested in the rear basin 153 of the head portion 151 of the body 150. A ledge 155 of the body portion 150 separates the rear basin 153 and the front basin 154. The stack of the seal layer 160, the PCB 31 and the mirror 20 nest in the rear basin 153 and are supported by the ledge 155 (which may be an annular ledge or a one or more separate ledge segments). The stack of the seal layer 160, the PCB 31 and the mirror 20 are secured to the head portion 151 by the light pipe 40 (while nesting in the rear basin 153). In the exemplified embodiment, the light transmissive elastomeric material 42 that forms the light pipe 40 both secures the stack (which includes the PCB 31 and the mirror 20) to the head portion 151 of the body 150 while also sealing the perimeter portion 22 of the mirror 20 and the rear surface 36 of the PCB 31. In certain embodiments, this is accomplished during the overmolding process in which the light pipe 40 is formed of the light transmissive elastomeric material 42 during injection molding.

In one embodiment, the seal layer 60 is secured to the ledge 155 so as to hermetically seal the rear basin 153 from the front basin 154. In an embodiment in which the seal layer 60 is formed of a thermoplastic elastomer, this can be accomplished by overmolding the seal layer 60 to the ledge 155 using an injection molding process. While the seal layer 60 is illustrated in the rear basin 153, in other embodiments the seal layer 60 is located within the front basin 154.

As mentioned above, a plurality of tooth cleaning elements 130 are provided on the head 120 of the oral care implement 100 and extend from a front surface 121 of the head 120. The front surface 121 and the rear surface 122 of the head 120 can take on a wide variety of shapes and contours, none of which are limiting of the present invention. For example, the front and rear surfaces 121, 122 can be planar, contoured or combinations thereof. The front surface 121 and rear surface 122 are bound by a peripheral or lateral surface.

The plurality of tooth cleaning elements 130 extend outward from the front surface 121 of the head 120 for cleaning contact with teeth. Common examples of "tooth cleaning elements" include, without limitation, filament bristles, fiber bristles, nylon bristles, spiral bristles, rubber bristles, elastomeric protrusions, flexible polymer protrusions, co-extruded filaments, flag bristles, crimped bristles, anti-bacterial bristles and combinations thereof and/or structures containing such materials or combinations. In one embodiment, the plurality of cleaning elements 130 comprises bristle tufts 131. In another embodiment, the plurality of cleaning elements 130 comprises both bristle tufts 131 and elastomeric elements.

In certain embodiments of the invention, the plurality of tooth cleaning elements 130 can be connected to the head portion 151 of the body 150 in any manner known in the art. For example, in-mold tufting (IMT) or stapling techniques could be used to mount the plurality of tooth cleaning elements 130 to the head portion 151 of the body 150. Alternatively, the tooth cleaning elements 130 could be mounted to tuft blocks or sections by extending through suitable openings in the tuft blocks so that the base of the tooth cleaning elements 130 are mounted within or below the tuft block.

In the exemplified embodiment, the plurality of tooth cleaning elements 130 are coupled to the head portion 151 of the body 150 using an AFT mounting method. In AFT, a head plate 171 (which can be a membrane in certain embodiments) is formed having a desired pattern of tuft holes 172. The head plate 171, in one embodiment, can be formed of any of the materials described above for the body 150. In one such embodiment, the head plate 171 is formed of one of the hard thermoplastics described above for the body 150 using an injection molding process. Once the head plate 171 is formed, a bristle tuft 131 (or other desired tooth cleaning element, such as an elastomeric element) is inserted into each of the tuft holes 172. When so inserted, a cleaning portion 132 of each of the bristle tufts 131 protrudes from a front surface 173 of the head plate 171 while an end portion protrudes from a rear surface 174 of the head plate 171. A heating element (such as a plate) is then brought into contact with the base portions of the bristle tufts 171 that melts the base portions of the bristle tufts 131, thereby fusing the base portions together to form a melt matte 175 (also known as a bristle melt in the art). Alternatively, the end portions of the bristle tufts 171 can be melted by any means known for applying heat thereto, such as convective heated gas flow and/or irradiation. When the melt matte 175 hardens, the bristles tufts 131 are secured to head plate 171 and cannot be pulled out though the front surface 173 of the head plate 171. As a result of the above, the head plate assembly 170 is formed. While the process is described above using bristle tufts 131, any type of tooth cleaning element 130 can be utilized to form the head plate assembly 170 as described above instead of or in combination with the bristle tufts.

Once the head plate assembly 170 is formed, the head plate assembly 170 is aligned with the front basin 154 in the head portion 151 of the body 150. The head plate assembly 170 is then nested into the front basin 154 (as shown in FIG. 4) and secured to the head portion 151 of the body 150. In one specific embodiment, the head plate 171 and the melt matte 175 are nested in the front basin 154 so that the head plate 171 contacts the ledge 155 of the body 150. Once so positioned, the head plate 171 is secured to the head portion 151 using a technique such as thermal welding, sonic welding, or adhesion. Of course, other connection techniques can be utilized, such as snap-fit, tight-fit, etc.

Figure 3:
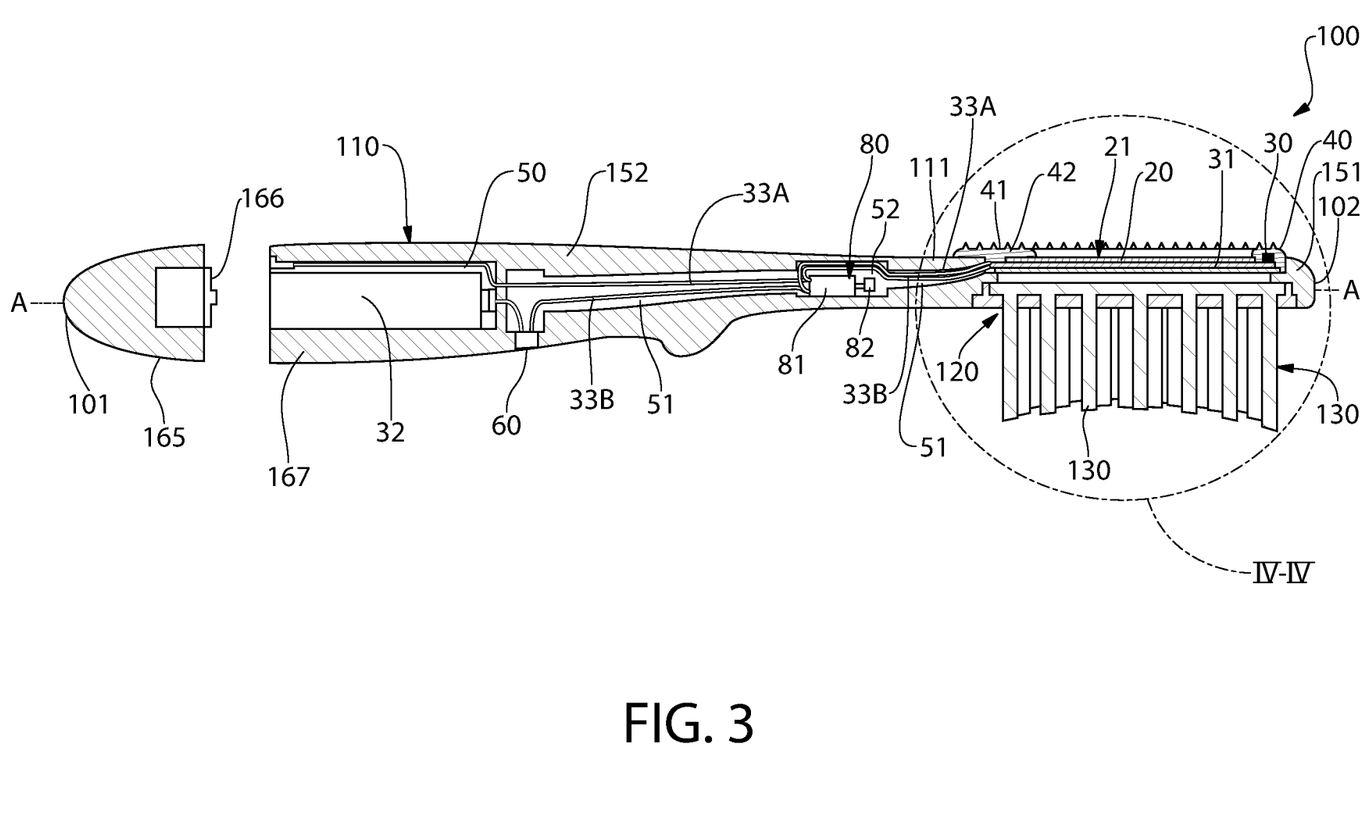
FIG. 3 is a longitudinal cross-sectional view of the oral care implement of FIG. 1 taken along the plane III-III of FIG. 1.

Referring now to FIGS. 3 and 4 concurrently, the handle portion 152 of the body 150 further comprises a cavity 50 in which a power source 32 is located. The power source 32 is operably coupled to the light source 30 so that illumination of the light source can be effectuated. In the exemplified embodiment, the power source 32 is operably coupled to the light source via wires 33A, 33B, which are in turn operably coupled to the PCB 31. The wires 33A, 33B extend through an internal longitudinal passageway 51 that extends through the handle portion 152. More specifically, the passageway 51 extends from the cavity 50 and terminates in an opening 52 in a sidewall 162 of the rear basin 153. The power source 32, in the exemplified embodiment, is a replaceable battery.

Of course, in other embodiments, the power source can be a rechargeable battery, a photovoltaic cell, or any other device capable of generating a suitable amount of electricity to power the light source 30. In one embodiment, the power source 32 can be an electro-dynamic cell that is charged by the mechanical action of the oral care implement 100 during use.

An actuator 60, in the form of an off/on button is provided in operable coupling between the power source 32 and the light source 30 so that illumination of the light source 30 can be controlled by the user. The actuator can be a slide button, a push button, a capacitive touch sensor, or any other type of actuator known in the art. The handle portion 152 of the body 150, in the exemplified embodiment, also comprises an end cap 165 that can be detachably coupled to a main body portion 167 of the handle portion 152 so that the power source 32 can be removed and/or replaced as necessary. An electrical contact 166 is provided on the end cap 165 so that upon the end cap 165 being coupled to the main body portion 167, the electrical circuit is complete and the light source 30 can be powered on and off by manipulation of the actuator 60.

In certain embodiments, such as the exemplified one, the oral care implement 100 further comprise a motion inducing element 80 for imparting motion to the head 120 of the oral care implement 100. The motion inducing element 80, in the exemplified embodiment, comprises a motor 81 and an eccentric 82 that is driven by the motor 81 to create vibrations that are transmitted to the head 120 of the oral care implement 100. Of course, other motion inducing elements can be used, including motor and drive coupling assemblies that move one or more tuft blocks on the head 120. The motion inducing element 80 is housed in a chamber 52 located within a thinned neck portion of the handle portion 152.

The motion inducing element 80 is operably coupled to the wires 33A, 33B and is powered by the power source 32. The motion inducing element 80 can be wired in series or in parallel with the light source 30. Furthermore, in certain embodiments, the electrical circuit is designed so that: (1) the light source 30 can be turned on independent of the motion inducing element 80 and vice versa by selective positioning of the actuator 60; and/or (2) the light source 30 and motion inducing element 80 can be turned on concurrently.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:
1. An oral care implement comprising:
a body comprising a handle portion and a head portion coupled to the handle portion, the body formed of a rigid material;

a mirror coupled to the head portion;

a light source coupled to the head portion adjacent the mirror;

a light transmissive elastomeric material coupled to the head portion and overlying the light source and the mirror, the light transmissive elastomeric material circumferentially surrounding the mirror such that a central portion of the mirror is exposed; and a plurality of soft tissue cleansing protuberances extending only from the light transmissive elastomeric material.

2. The oral care implement according to claim 1 wherein the light transmissive elastomeric material acts as a light pipe to distribute the light emitted by the light source along the light transmissive elastomeric material for emission from the light transmissive elastomeric material.

3. The oral care implement according to claim 1 wherein the light transmissive elastomeric material comprises a ring of the light transmissive elastomeric material that circumferentially surrounds the mirror.

4. The oral care implement according to claim 1 wherein the light transmissive elastomeric material secures the mirror to the body.

5. The oral care implement according to claim 1 wherein the light source is embedded in the light transmissive elastomeric material.

6. The oral care implement according to claim 1 wherein the light transmissive elastomeric material comprises the plurality of protuberances.

7. The oral care implement according to claim 1 wherein the light transmissive elastomeric material comprises a convex outer surface.

8. The oral care implement according to claim 1 further comprising a printed circuit board, the mirror positioned on the printed circuit board and the light transmissive elastomeric material sealing a rear surface of the printed circuit board, and wherein the light source is operably coupled to the printed circuit board.

9. The oral care implement according to claim 8 further comprising a seal layer on the printed circuit board that seals a front surface of the printed circuit board.

10. The oral care implement according to claim 1 further comprising a plurality of tooth cleaning elements extending from a front surface of the head portion of the oral care implement, and wherein the first surface of the mirror is a reflective surface that forms a rear surface of the head portion opposite the front surface of the head portion.

11. The oral care implement according to claim 10 further comprising a rear basin formed in the head portion of the body, the mirror nested within the rear basin.

12. The oral care implement according to claim 11 further comprising a front basin formed in the head portion, and wherein the plurality of tooth cleaning elements are secured to a head plate via anchor free tufting to form a head plate assembly, the head plate assembly nesting within the front basin and secured to the head portion of the body.

13. The oral care implement according to claim 12 wherein the front basin and the rear basin collectively form a through-hole in the head portion of the body.

14. An oral care implement comprising:
a body comprising a handle portion and a head portion, the head portion coupled to the handle portion;
a mirror coupled to the head portion;
a light source coupled to the head portion; and
a light pipe formed of a light transmissive elastomeric material coupled to a rear surface of the head portion and surrounding the mirror, the light pipe operably coupled to the light source to distribute light emitted by the light source through the light pipe and the light pipe overlying the mirror and circumferentially surrounding the mirror;
wherein only the light pipe comprises a plurality of protuberances for cleansing soft tissue.

15. The oral care implement according to claim 14 wherein the light pipe forms a ring that circumferentially surrounds the mirror.

16. The oral care implement according to claim 14 wherein the light source is embedded in the light pipe.

17. The oral care implement according to claim 14 further comprising a plurality of tooth cleaning elements extending from a front surface of the head portion of the oral care implement, and wherein a reflective surface of the mirror forms the rear surface of the head portion of the oral care implement opposite the front surface of the head.

18. The oral care implement according to claim 14 further comprising: a rear basin formed in the head portion of the body, the mirror nested within the rear basin; and a front basin formed in the head portion of the body, and wherein the plurality of tooth cleaning elements are secured to a head plate via anchor free tufting to form a head plate assembly, the head plate assembly nesting within the front basin and secured to the head portion.

19. An oral care implement comprising:
a body comprising a handle portion and a head portion, the head portion coupled to the handle portion through a neck portion;
a plurality of tooth cleaning elements extending from a front surface of the head portion, the plurality of tooth cleaning elements secured to a head plate that is nested within a front basin formed in the front surface of the head portion;
a mirror nested within a rear basin formed into a rear surface of the head portion, the rear surface of the head portion opposite the front surface of the head portion;
a light source coupled to the head portion adjacent the mirror; and
a light transmissive elastomeric material coupled to the rear surface of the head portion, overlying the light source, and overlying and circumferentially surrounding the mirror;
wherein the front basin and the rear basin are connected to form a through-hole in the head portion of the body; and
wherein only the light transmissive elastomeric material comprises a plurality of soft tissue cleansing protuberances.

20. The oral care implement of claim 1 wherein the light transmissive elastomeric material extends onto the neck portion of the body, at least one protuberance of the plurality of protuberances positioned on the neck portion of the body.

* * * * *